United States Patent [19]

Guillon et al.

[11] 4,425,326

[45] Jan. 10, 1984

[54] ANHYDROUS NAIL VARNISHES

[75] Inventors: Michel Guillon, Bourg-La-Reine; Jean Mondet, Sevran; Christos Papantoniou, Montmorency; Claudine Vandenbossche, Aulnay-Sous-Bois, all of France

[73] Assignee: Societe Anonyme dite : L'Oreal, Paris, France

[21] Appl. No.: 247,207

[22] Filed: Mar. 24, 1981

[30] Foreign Application Priority Data

Apr. 1, 1980 [FR] France ................. 80 07328

[51] Int. Cl.³ .................. C08F 20/06; C08F 20/56; A61K 7/04
[52] U.S. Cl. ..................... 424/61; 526/287; 526/307.6; 526/317
[58] Field of Search ............... 424/61; 526/317, 303

[56] References Cited

U.S. PATENT DOCUMENTS

| | | | |
|---|---|---|---|
| 2,996,471 | 8/1961 | Reter | 424/180 |
| 3,478,756 | 11/1969 | Sautter et al. | 424/61 |
| 3,804,784 | 4/1974 | Wycliffe | 260/14 |
| 3,927,203 | 12/1975 | Seymour et al. | 424/61 |
| 4,085,264 | 4/1978 | Seib et al. | 526/317 |
| 4,126,675 | 11/1978 | Boulogne et al. | 424/61 |
| 4,289,752 | 9/1981 | Mahieu et al. | 424/81 |

FOREIGN PATENT DOCUMENTS

| | | |
|---|---|---|
| 1504440 | 10/1967 | France . |
| 2119904 | 7/1971 | France . |
| 2180006 | 4/1973 | France . |
| 2205557 | 10/1973 | France . |
| 78679 | 12/1977 | Luxembourg . |
| 1074201 | 5/1964 | United Kingdom . |

OTHER PUBLICATIONS

Edwin Sidi, "Problemes Capillaires", copyright 1966, pp. 178–183.
Hilbot, "Handbook of Cosmetic Science", Pergamon Press, 1963, p. 321.
Harry, "Harry's Cosmeticology", Leonard Hill Books An Intertext Publisher, pp. 410–414.
Rapport De Recherche (FR 80 07 328) (FA 242 648).

*Primary Examiner*—Delbert R. Phillips
*Assistant Examiner*—F. T. Moezie
*Attorney, Agent, or Firm*—Parkhurst & Oliff

[57] ABSTRACT

Anhydrous nail varnishes are disclosed which contain a copolymer of:

(1) at least one unsaturated polar monomer of the formula:

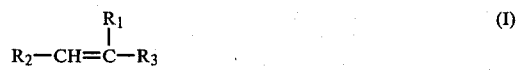

(I)

in which: $R_1$ represents H, —$CH_3$ or —$CH_2COOH$; such that if $R_1$ represents H, $R_2$ represents either (a) H, in which case $R_3$ represents:

(i) —COOH (ii) —$SO_3H$

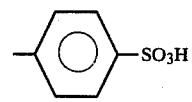

(iii)

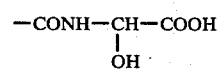

(iv)

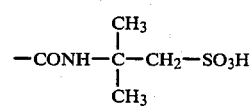

(v)

or (vi) —$COOR_4$, $R_4$ representing a glycidyl radical, a mono- or di-hydroxy-alkyl radical, the alkyl radical having from 2 to 4 carbon atoms, or the radical —(C$H_2$—$CH_2$—C)l—R', R' representing a methyl or ethyl radical and l representing 3 or 4, or (b) —COOH, in which case $R_3$ represents:

(vii) —$CO_2R_5$ or (viii) —$CONHR_5$ $R_5$ representing H or an alkyl radical having from 1 to 4 carbon atoms; and if $R_1$ represents —$CH_3$ or —$CH_2COOH$, $R_2$ represents H and $R_3$ represents —COOH or —$COOR_4$;

(2) at least one methacrylate monomer of the formula:

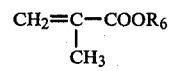

(II)

in which: $R_6$ represents a linear or branched alkyl radical having up to 18 carbon atoms, or the radical

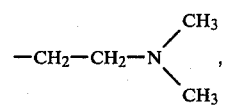

and (3) at least one acrylate monomer of the formula:

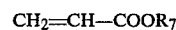

(III)

in which: $R_7$ represents a linear or branched alkyl radical having up to 18 carbon atoms, or a quaternary derivative thereof.

9 Claims, No Drawings

ANHYDROUS NAIL VARNISHES

The present invention relates to manicure products and in particular to anhydrous colourless or coloured nail varnishes which have good stability over time, a good gloss and excellent adhesion to nail keratin.

The main characteristics which nail varnishes must possess are essentially that they are not aggressive towards the skin and the nails, that they are convenient to apply, that they are stable on storage, that is to say have a good homogeneity and a good stability with time, and finally that they give a film having satisfactory characteristics.

These characteristics of the film are essentially the production of a uniform thickness and a good gloss, which implies a smooth application surface, excellent adhesion to the nail and a satisfactory flexibility in order to prevent the varnish from breaking or crumbling.

On the whole, nail varnish compositions have remained substantially unchanged for a certain number of years and are essentially based on the use of a polymer mixture consisting of nitrocellulose and a low molecular weight arylsulphonamide/formaldehyde resin known by the name SANTOLITE.

In fact, if nitrocellulose is used by itself as a film-forming agent, the films obtained are brittle and have poor adhesion to the nail.

The SANTOLITE thus makes it possible to plasticise the nitrocellulose film and to ensure good adhesion of the varnish to the nail.

However, it has been recommended to replace the nitrocellulose by certain copolymers, in particular acrylate/methacrylate copolymers or also methyl methacrylate/hexyl methacrylate copolymers, such as those described in French Pat. No. 76/14430.

The use of these copolymers has made it possible to reduce and, in certain cases, even to dispense totally with, the conventional film-forming agents without thereby producing a deterioration in the properties of the film obtained. It was noted, however, that the adhesion was not always satisfactory.

By using polymers containing a certain percentage of units of unsaturated monomers carrying at least one polar group, and more particularly a carboxylic or sulphonic acid group, it has been found, according to the present invention, that it is possible to overcome the disadvantages of the copolymers previously used.

The copolymers used in the nail varnishes according to the invention thus make it possible to partially or totally replace the nitrocellulose and/or the resin of the arylsulphonamide/formaldehyde type. This itself represents an advantage by virtue of a lower cast price and of a reduction in the risks involved in handling nitrocellulose and formaldehyde-based resins.

The present invention provides an anhydrous nail varnish which is characterised in that it contains, in a solvent system for varnishes, a resin essentially consisting of a copolymer resulting from the copolymerisation of:

(1) at least one unsaturated polar monomer of the formula:

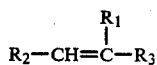  (I)

in which: $R_1$ represents H, $-CH_3$ or $-CH_2COOH$ such that if $R_1$ represents H, $R_2$ represents:
(a) either H, in which case $R_3$ represents:
 (i) $-COOH$
 (ii) $-SO_3H$

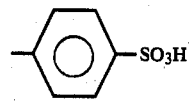  (iii)

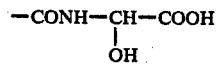  (iv)

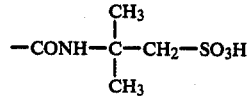  (v)

or
 (vi) $-COOR_4$, $R_4$ representing a glycidyl radical, a mono- or di-hydroxyalkyl radical, the alkyl radical having from 2 to 4 carbon atoms, or the radical $-(CH_2-CH_2-O)_l-R'$, $R'$ representing a methyl or ethyl radical and $l$ representing 3 or 4,
(b) or $-COOH$, in which case $R_3$ represents:
 (vii) $-CO_2R_5$ or
 (viii) $-CONHR_5$ $R_5$ representing H or an alkyl radical having from 1 to 4 carbon atoms; if $R_1$ represents $-CH_3$ or $-CH_2COOH$, $R_2$ represents H and $R_3$ represents $-COOH$ or $-COOR_4$;

(2) at least one methacrylate of the formula:

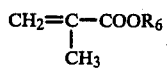  (II)

in which: $R_6$ represents a linear or branched alkyl radical having from 1 to 18 carbon atoms, or the radical

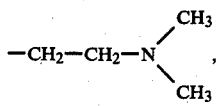

and
(3) at least one acrylate of the formula:

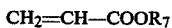  (III)

in which: $R_7$ represents a linear or branched alkyl radical having from 1 to 18 carbon atoms.

These copolymers preferably consist of:
(1) 5 to 30%, and especially 8 to 20%, by weight of at least one polar monomer of the formula (I),
(2) 1 to 90%, and especially 5 to 85%, by weight of at least one methacrylate of the formula (II), and
(3) 1 to 90%, and especially 5 to 85%, by weight of at least one acrylate of formula (III).

These copolymers are usually terpolymers but can also be tetrapolymers, pentapolymers or higher polymers insofar as more than one of the monomers from each of the three groups mentioned above is used.

Furthermore, according to a particular embodiment of the invention, the copolymers can also result from the copolymerisation of other monomers in addition to those defined above, such as N-vinylpyrrolidone or acrylamides or methacrylamides of the formula:

in which: $R_8$ represents H or $-CH_3$ and $R_9$ represents H, $-CH_2OH$,

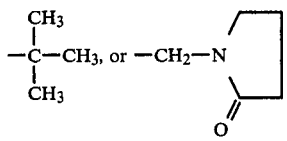

According to this embodiment, the percentage by weight of these additional monomers is suitably 1 to 20% by weight and preferably 2 to 15% by weight.

The following may be mentioned more particularly as monomers corresponding to formula (I): acrylic acid, methacrylic acid, maleic acid, itaconic acid, vinylsulphonic acid, styrene-4-sulphonic acid, acrylamidoglycolic acid, 2-acrylamido-2-methylpropyl-1-sulphonic acid, monobutyl maleate, monoethyl maleate, maleamic acid, N-butylmaleamic acid, glycidyl acrylate, 2,3-dihydroxypropyl acrylate, 2-hydroxyethyl acrylate, 3-hydroxypropyl acrylate, ω-methyl- or ω-ethyl-(polyethylene glycol) acrylate and the corresponding methacrylates.

The following may be mentioned amongst the monomers of formula (II): methyl, ethyl, butyl, tert.-butyl, hexyl, dodecyl and octadecyl methacrylates and 2-N,N-dimethylamino-ethyl methacrylate.

The following may be mentioned amongst the monomers of formula (III): methyl, ethyl, butyl, 2-ethylhexyl, dodecyl and octadecyl acrylates.

Finally, the following may be mentioned amongst the additional monomers corresponding to formula (IV): acrylamide, methacrylamide, N-tert.-butylacrylamide N-hydroxymethylacrylamide and N-[(N'-pyrrolidone-2)-methyl]acrylamide.

The presence of at least one monomer carrying either a free or esterified carboxylic acid group or a sulphonic acid group has proved essential for imparting good properties to the copolymers for the nail varnishes, and especially for good adhesion.

However, certain acids, such as crotonic acid or allyloxyacetic acid, cannot be used because their copolymerisation with acrylic or methacrylic acid esters, such as those of formulae (II) and (III), is virtually impossible using the normal methods of polymerisation.

The copolymers used in the invention generally have a molecular weight of 2,000 to 200,000 and preferably 10,000 to 100,000, measured by osmometry.

The copolymers which can be used in the varnish compositions according to the invention can be obtained by various conventional polymerisation processes, such as suspension polymerisation, bulk polymerisation, emulsion polymerisation or solution polymerisation. As the nail varnishes according to the invention are to be anhydrous, the polymerisation is in consequence preferably carried out in solution in an organic solvent, such as ethyl acetate, butyl acetate or acetone.

According to this solution polymerisation process, the catalysts used are typically peroxides, peresters and percarbonates, in particular benzoyl peroxide, di-tert.-butyl peroxide, 2-tert.-butyl-peroxyethyl hexanoate, 4-bis-tert.-butylcyclohexyl peroxydicarbonate, or azobis-isobutyronitrile.

It is also possible to use oxidation/reduction systems as the initiator or to subject the reaction mixture to irradiation in order to produce free radicals.

The reaction time is generally 2 to 24 hours at a temperature of 25° to 80° C.

After the polymerisation reaction has ended, the copolymer can be obtained by precipitation with a solvent in which the polymer is not soluble, such as petroleum ether or certain solvent mixtures.

The amount of polymerisation catalyst is suitably 0.3 to 6%, relative to the total weight of the monomers used for the reaction.

If the copolymers used in the invention contain tertiary amine groups, such as those which can result from the copolymerisation of 2-N,N-dimethylaminoethyl methacrylate, the said groups can be quaternised with a quaternising agent, such as dimethylsulphate or ethyl bromide.

Finally, it should be noted that certain functional groups can be introduced into the copolymers by subsequent reaction with suitable reactants.

Thus, if it is desired to obtain a copolymer containing units derived from a monoalkyl maleate, it is possible to carry out the copolymerisation starting from maleic anhydride and then to react the product with the appropriate amount of alcohol to obtain partial esterification of the anhydride groups of the copolymer.

Similarly, if it is desired to obtain units derived from maleamides or from N-alkyl-substituted maleamides, it is possible to react ammonia or an amine with the anhydride groups of the copolymer.

Various examples of the preparation of the copolymers which can be used according to the invention are described below.

Whether coloured or colourless, the nail varnishes according to the invention preferably contain from 3 to 35% by weight of a copolymer as defined above, the remainder essentially consisting of the solvent system of the varnish, that is to say the customary solvents and/or conventional diluents for this type of composition.

However, the varnishes preferably also contain from, say, 0.2 to 10% by weight of at least one plasticiser, in order to improve the adhesion and the flexibility of the film.

The following may be mentioned amongst the plasticisers: tricresyl phosphate, benzyl benzoate, tributyl phosphate, butyl acetylricinoleate, glyceryl acetylricinoleate, dibutyl phthalate, butyl glycolate, dioctyl phthalate, butyl stearate, tributoxyethyl phosphate, triphenyl phosphate, triethyl citrate, tributyl citrate, tributyl acetylcitrate, 2-triethylhexyl acetylcitrate, dibutyl tartrate, dimethoxyethyl phthalate, diisobutyl phthalate, diamyl phthalate, camphor and various mixtures thereof.

Although, with the nail varnishes according to the invention, it is possible to dispense with using nitrocellulose and/or a resin of the arylsulphonamide/formaldehyde type, it is possible to introduce them into the formulations, albeit in a substantially lower proportion than that which is commonly employed.

The nitrocelluloses are typically of the "RS" or "SS" type, in particular ¼ second RS type nitrocellulose, ½ second RS type nitrocellulose and RS ¾ second type nitrocellulose.

The nitrocelluloses of the "RS" type are preferably used according to the invention.

The resins of the arylsulphonamide/formaldehyde type are those known by the tradenames "Santolite MHP" and "Santolite MS 80%", the former being the harder, the latter leading to the formation of films of greater flexibility.

As has been stated, the nail varnishes according to the invention are anhydrous, so that the solvent system is produced from organic solvents or mixtures thereof. This makes it possible to obtain relatively short drying times. The following may be mentioned amongst the solvents: acetone, ethyl acetate, butyl acetate, 2-methoxyethyl acetate, methyl ethyl ketone, methyl isobutyl ketone and methyl acetate.

Furthermore, the solvent system may also comprise a diluent, preferably an aromatic organic solvent, such as toluene or xylene, in a proportion which is generally from 10 to 30%, relative to the total weight of the varnish.

The varnishes can also contain other volatile solvents, such as ethanol, n-butanol, n-propanol, isopropanol or mixtures thereof, these volatile solvents being employed more particularly in the case where the varnishes contain a certain amount of nitrocellulose.

If they are to be coloured, the nail varnishes according to the invention contain at least one organic or inorganic colourant. The following may be mentioned amongst the organic colourants: D and C RED Nos. 10, 11, 12 and 13, D and C RED No. 7, D and C RED Nos. 5 and 6, D and C RED No. 34 and lakes, such as the lake D and C YELLOW No. 5 and the lake D and C RED No. 2. The following may be mentioned amongst the inorganic colourants: titanium dioxide, bismuth oxychloride, brown iron oxide, red iron oxides and also guanine.

These colourants are preferably present in the varnishes in an amount of 0.1 to 8% by weight, relative to the total weight of the composition. The varnishes according to the invention can also contain other ingredients, such as products which make it possible to avoid sedimentation, and especially clays of the montmorillonite type, such as "Bentone 27" or "Bentone 38", in the presence of a swelling agent, such as orthophosphoric acid.

The following Examples further illustrate the present invention and the preparation of the copolymers used in the varnish compositions according to the invention.

EXAMPLE 1

Copolymer of acrylic acid, 20%/butyl methacrylate, 40%/ethyl acrylate, 40%.

40 g of butyl methacrylate, 40 g of ethyl acrylate, 20 g of acrylic acid, 2 g of azo-bis-isobutyronitrile, crystallised from ethanol, and 100 g of ethyl acetate are placed in a 500 cm$^3$ round-bottomed flask fitted with a mechanical stirrer, a condenser and a nitrogen inlet tube.

After stirring, the reaction mixture is heated under reflux for 16 hours. After cooling, the solution is diluted with 100 g of ethyl acetate and the polymer is then precipitated by adding 7 liters of petroleum ether. After drying, the expected polymer is obtained with a yield of 80%.

Viscosity: 1.4 cPo (in 5% strength solution in ethyl acetate at 35.4° C.).

Following the same procedure as that described in Example 1 above, the copolymers of Examples 2 to 23, summarised in Table I and II below, were also prepared:

TABLE I

| Monomers | Ex 2 | Ex 3 | Ex 4 | Ex 5 | Ex 6 | Ex 7 | Ex 8 | Ex 9 | Ex 10 | Ex 11 | Ex 12 |
|---|---|---|---|---|---|---|---|---|---|---|---|
| Acrylic acid | | | | | .10 | 3 | | 2 | | | 10 |
| Methacrylic acid | 20 | 10 | 10 | 10 | | | | | | | |
| Styrene-4 sulphonic acid | | | | | | | | | 5 | | |
| 2-acrylamido-2 methyl-propyl-1-sulphonic acid | | | | | | | | | | 8 | |
| Maleic acid | | | | | | | | | | | 5 |
| Acrylamidoglycolic acid | | | | | | | 10 | | | | |
| Methyl methacrylate | | | | | | | | | 60 | | 60 |
| Butyl methacrylate | 40 | 30 | 60 | 45 | 60 | 57 | 30 | 60 | | 55 | |
| Ethyl acrylate | 40 | 60 | 30 | 45 | 30 | 30 | 60 | 28 | 2 | | 20 |
| Hexyl methacrylate | | | | | | | | | 33 | | |
| Dodecyl methacrylate | | | | | | | | | | | 5 |
| Methyl acrylate | | | | | | | | | | 37 | |
| Methacrylamide | | | | | | | | 10 | | | |
| N—Hydroxymethacrylamide | | | | | | 10 | | | | | |
| Yield % | 76 | 85 | 78 | 80 | 70 | 65 | 76 | 78 | 74 | 82 | 70 |
| Viscosity (cPo) (5% strength solution in ethyl acetate at 35,4° C.) | 1,3 | 1,6 | 1,4 | 1,7 | 1,6 | 1,6 | 1,4 | 1,5 | 1,6 | 1,7 | 1,5 |

TABLE II

| Monomers | Ex 13 | Ex 14 | Ex 15 | Ex 16 | Ex 17 | Ex 18 | Ex 19 | Ex 20 | Ex 21 | Ex 22 | Ex 23 |
|---|---|---|---|---|---|---|---|---|---|---|---|
| Acrylic acid | | | 25 | 5 | | | 15 | 10 | | | 20 |
| Methacrylic acid | 10 | 5 | | | 8 | 3 | | | 10 | 15 | |
| Maleic acid | | | | | | | | | 5 | | |
| Monobutyl maleate | 3 | | | | | | | | | | |
| N—vinyl pyrrolidone | | 5 | | | | | | | | | |
| N—[N—pyrrolidone-2)- | | | | | | 5 | | | | | |

TABLE II-continued

| Monomers | Ex 13 | Ex 14 | Ex 15 | Ex 16 | Ex 17 | Ex 18 | Ex 19 | Ex 20 | Ex 21 | Ex 22 | Ex 23 |
|---|---|---|---|---|---|---|---|---|---|---|---|
| methyl]acrylamide | | | | | | | | | | | |
| Methyl methacrylate | | 70 | 63 | 64 | 55 | | 70 | 80 | | 45 | |
| Butyl methacrylate | 50 | | | | | 55 | | | 65 | | 45 |
| Hexyl methacrylate | 33 | | | 29 | | | | | | | |
| 2-N,N—dimethylamino-ethyl methacrylate | | | | | 3 | | | | | | |
| Ethyl acrylate | | | 2 | 2 | 34 | 37 | | | 20 | | |
| Methyl acrylate | | | | | | | | | | 4 | |
| Hexyl acrylate | 4 | 15 | | | | | 15 | | | 36 | 30 |
| Dodecyl acrylate | | 5 | | | | | | 10 | | | |
| N—tert.-butylacrylamide | | | | | | | | | | | 5 |
| Yield % | 78 | 78 | 75 | 80 | 75 | 75 | 74 | 76 | 74 | 70 | 72 |
| Viscosity (cPo) (5% strength solution in ethyl acetate at 35,4° C.) | 1,8 | 1,4 | 1,6 | 1,6 | 1,5 | 1,6 | 1,7 | 1,5 | 1,6 | 1,5 | 1,7 |

Examples of nail varnishes

EXAMPLE A

A colourless nail varnish is prepared according to the invention by mixing the following ingredients:
Copolymer of Example 1—25 g
Butyl phthalate—3 g
Camphor—2 g
Ethyl acetate—30 g
Butyl acetate—40 g On applying this varnish to the nails with a paintbrush, a uniform layer is obtained which, after drying, has good adhesion and an excellent gloss.

EXAMPLE B

A coloured nail varnish is prepared according to the invention by mixing the following ingredients:
Copolymer of Example 2—25 g
Butyl phthalate—2 g
Ethyl acetate—20 g
Toluene—20 g
Bentone 27—1.5 g
Phosphoric acid—0.02 g
Titanium oxide—0.75 g
Brown iron oxide—0.25 g
D and C RED 7-calcium lake—0.5 g
D and C RED 34—0.3 g
D and C YELLOW 5-aluminium lake—0,7 g
Butyl acetate q.s.p.—100 g

EXAMPLE C

A coloured nail varnish is prepared according to the invention by mixing the following ingredients:
Copolymer prepared according to Example 30—20 g
Santolite MHP—5 g
Camphor—1 g
Triethyl citrate—3 g
Ethyl acetate—15 g
Toluene—20 g
Bentone 27—1.2 g
Citric acid—0.05 g
Titanium oxide—0.3 g
Brown iron oxide—0.2 g
Prussian Blue—0.1 g
D and C RED 7-calcium lake—0.3 g
D and C YELLOW 5-aluminium lake—0.7 g
Butyl acetate q.s.p.—100 g On applying this varnish to the nails, the varnish was observed to have very good adhesion and an excellent gloss.

EXAMPLE D

Copolymer of Example 2—8 g
½ second nitrocellulose—12 g
Ethyl alcohol—3 g
Butyl alcohol—3 g
Camphor—4 g
Butyl acetylricinoleate—8 g
Ethyl acetate—12 g
Toluene—25 g
Methyl ethyl ketone—2 g
Bentone 27—1.4 g
Phosphoric acid—0.01 g
Brown iron oxide—0.5 g
D and C RED 7-calcium lake—0.3 g
D and C RED 6-barium lake—0.2 g
Bismuth oxychloride—0.8 g
Butyl acetate q.s.p.—100 g

EXAMPLE E

A coloured nail varnish is prepared according to the invention by mixing the following ingredients:
Copolymer of Example 4—5 g
Santolite MHP—5 g
½ second nitrocellulose—12 g
Isopropyl alcohol—3 g
Butyl alcohol—3 g
Camphor—1 g
Tricresyl phosphate—3 g
2-Methoxyethyl acetate—5 g
Ethyl acetate—12 g
Toluene—18 g
Bentone 27—2 g
Titanium oxide—0.5 g
Prussian Blue—0.2 g
D and C YELLOW 5-aluminium lake—0.5 g
D and C RED 9—0.3 g
D and C RED 11—0.4 g
Butyl acetate q.s.p.—100 g

EXAMPLE F

A colourless nail varnish is prepared according to the invention by mixing the following ingredients:
Copolymer of example 10—23 g
Butyl phthalate—3 g
Camphor—2 g
Ethyl acetate—30 g
Butyl acetate—40 g In this example which gives rise to a film with good adhesion and excellent gloss, the copolymer of example 10 can be replaced by one of the copolymers of examples 11, 14, 17, 18 and 23.

EXAMPLE G

A coloured nail varnish is prepared according to the invention by mixing the following ingredients:
Copolymer of example 4—6 g
½ second nitrocellulose—10 g
Ethyl alcohol—3 g
Butyl alcohol—3 g
Camphor—4 g
Butyl acetylricinoleate—8 g
Ethyl acetate—14 g
Toluene—23 g
Methyl ethyl ketone—2 g
Bentone 27—1,4 g
Phosphoric acid—0,01 g
Brown iron oxide—0,5 g
D and C RED 7-calcium lake—0,3 g
D and C RED 6-barium lake—0,2 g
Bismuth oxychloride—0,8 g
Butyl acetate q.s.p.—100 g In this example the copolymer of example 12 can be advantageously replaced by the same quantity of one the copolymers of examples 13, 15, 16 and 19 at 22.

We claim:

1. A substantially anhydrous nail varnish which contains in an organic solvent system for varnish from 3 to 35% by weight of a copolymer resulting from the copolymerization of:
   (1) 5 to 30% by weight of at least one unsaturated polar monomer of the formula:

   (I)

in which: $R_1$ represents H, $-CH_3$ or $-CH_2COOH$; such that if $R_1$ represents H, $R_2$ represents either
   (a) H, in which case $R_3$ represents:
      (i) —COOH
      (ii) —$SO_3H$

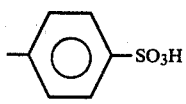 (iii)

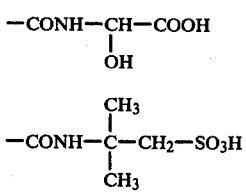 (iv), (v)

or
      (vi) —$COOR_4$,
   $R_4$ representing a glycidyl radical, a mono- or dihydroxyalkyl radical, the alkyl radical having from 2 to 4 carbon atoms, or the radical $-(CH_2-CH_2-O)l-R'$, $R'$ representing a methyl or ethyl radical and l representing 3 or 4, or
   (b) —COOH, in which case $R_3$ represents:
      (vii) —$CO_2R_5$ or
      (viii) —$CONHR_5$ $R_5$ represents H or an alkyl radical having from 1 to 4 carbon atoms; and if $R_1$ represents $-CH_3$ or $-CH_2COOH$, $R_2$ represents H and $R_3$ represents —COOH or —$COOR_4$;
   (2) 1 to 90% by weight of at least one methacrylate monomer of the formula:

 (II)

in which: $R_6$ represents a linear or branched alkyl radical having up to 18 carbon atoms, or the radical

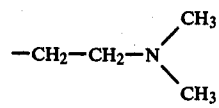

and
   (3) 1–90% by weight of at least one acrylate monomer of the formula:

 (III)

in which: $R_7$ represents a linear or branched alkyl radical having up to 18 carbon atoms, said copolymer having a molecular weight of 10,000 to 200,000 measured by osmometry.

2. A varnish according to claim 1 in which the said polymer is derived from:
   (1) 8 to 20% by weight of at least one polar monomer of formula (I),
   (2) 5 to 85% by weight of at least one methacrylate monomer of formula (II), and
   (3) 5 to 85% by weight of at least one acrylate monomer of formula (III).

3. A varnish according to claim 1 in which the copolymer is also derived from at least one other monomer which is N-vinylpyrrolidone or an acrylamide or methacrylamide of the formula:

 (IV)

in which: $R_8$ represents H or $-CH_3$ and $R_9$ represents H, $-CH_2OH$,

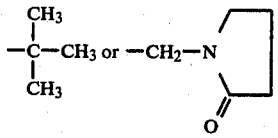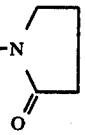

in an amount of 1 to 20% by weight relative to the total weight of the monomers.

4. A varnish according to claim 3 in which the said other monomer is used in an amount from 2 to 15% by weight relative to the total weight of the monomers.

5. A varnish according to claim 3 in which the acrylamide or methacrylamide of the formula (IV) is acrylamide, methacrylamide, N-tert.-butylacrylamide, N-hydroxymethacrylamide or N-[(N'-pyrrolidone-2)-methyl]acrylamide.

6. A varnish according to claim 1 in which the unsaturated polar monomer of formula (I) is acrylic acid, methacrylic acid, maleic acid, itaconic acid, vinylsulphonic acid, styrene-4-sulphonic acid, acrylamidoglycolic acid, 2-acrylamido-2-methylpropyl-1-sulphonic acid, monobutyl maleate, monoethyl maleate, maleamic acid, N-butylmaleamic acid, or glycidyl, 2,3-dihydroxy-propyl, 2-hydroxyethyl, 3-hydroxypropyl, ω-methyl- or ω-ethyl-(polyethylene glycol) acrylate or methacrylate.

7. A varnish according to claim 1 in which the methacrylate monomer of formula (II) is methyl, ethyl, butyl, tert.-butyl, hexyl, dodecyl or octadecyl methacrylate or 2-N,N-dimethylamino-ethyl methacrylate.

8. A varnish according to claim 1 in which the acrylate of formula (III) is methyl, ethyl, butyl, 2-ethylhexyl, dodecyl or octadecyl acrylate.

9. A varnish according to claim 1, in which said polymer is quaternized with a quaternizing agent selected from the group consisting of dimethyl sulphate and ethyl bromide.

* * * * *